(12) United States Patent
Cazares Delgadillo

(10) Patent No.: US 10,946,191 B2
(45) Date of Patent: Mar. 16, 2021

(54) IONTOPHORETIC DEVICE HAVING A RESERVOIR

(71) Applicant: L'OREAL, Paris (FR)

(72) Inventor: Jennyfer Cazares Delgadillo, Chevilly-Larue (FR)

(73) Assignee: L'OREAL, Paris (FR)

( * ) Notice: Subject to any disclaimer, the term of this patent is extended or adjusted under 35 U.S.C. 154(b) by 1034 days.

(21) Appl. No.: 15/106,226

(22) PCT Filed: Dec. 8, 2014

(86) PCT No.: PCT/EP2014/076829
§ 371 (c)(1),
(2) Date: Jun. 17, 2016

(87) PCT Pub. No.: WO2015/091044
PCT Pub. Date: Jun. 25, 2015

(65) Prior Publication Data
US 2016/0310728 A1    Oct. 27, 2016

(30) Foreign Application Priority Data
Dec. 20, 2013   (FR) ........................................ 1363283

(51) Int. Cl.
*A61N 1/30*    (2006.01)
*A61N 1/04*    (2006.01)
(Continued)

(52) U.S. Cl.
CPC ........... *A61N 1/303* (2013.01); *A45D 34/041* (2013.01); *A61M 37/00* (2013.01); *A61N 1/0428* (2013.01); *A61M 2037/0007* (2013.01)

(58) Field of Classification Search
CPC ........ A61N 1/025; A61N 1/0428; A61N 1/04; A61N 1/0404; A61N 1/0412;
(Continued)

(56) References Cited
U.S. PATENT DOCUMENTS 3,095,598 A * 7/1963 Gonnella ............. A45D 34/041
401/213
6,766,192 B1 * 7/2004 D'Africa ................ A61N 1/303
604/20
(Continued)

FOREIGN PATENT DOCUMENTS

CN           101532190 A      9/2009
DE    102007030670 A1 *  1/2009   ............. A45D 44/22
(Continued)

OTHER PUBLICATIONS

International Search Report for PCT/EP2014/076824, dated Feb. 6, 2015.
(Continued)

*Primary Examiner* — Rachel T Sippel
*Assistant Examiner* — Benjamin M. Kusiak
(74) *Attorney, Agent, or Firm* — The Marbury Law Group, PLLC

(57) ABSTRACT

A device for the cosmetic treatment of keratin materials with an electric current, including: a current generator (1), a reservoir (3) containing a cosmetic composition (P), an end piece (2) comprising an electrode (4) and at least one applicator member (6, 7), said applicator member (6, 7) delimiting an outer wall (61, 71) that is able to be filled with product contained in the reservoir (3), a counter electrode (5), a system for regulating the quantity of composition (P) exiting the reservoir (3) on the basis of the impedance measured between the electrode (4) and the keratin materials, the electrode (4) and the applicator member (6, 7) being designed such that the composition (P) is the only conductive substance in contact with the skin while the device is being used.

17 Claims, 2 Drawing Sheets

(51) Int. Cl.
*A45D 34/04* (2006.01)
*A61M 37/00* (2006.01)

(58) Field of Classification Search
CPC .... A61N 1/0448; A61N 1/0476; A61N 1/048;
A61N 1/18; A61N 1/30; A61N 1/303;
A61N 1/32; A61N 1/325; A61N
1/326–328; A61N 1/36014; A61N
1/36031; A61N 1/36034; A61N 5/0625;
A61N 5/06; A61N 5/0616; A61N 5/0617;
A61N 2005/0659; A61M 35/00; A61M
35/003; A61M 2205/051; A61M
2205/054; A61M 2205/055; A61M
2205/103; A61M 2205/3317; A61M
2205/3327; A61M 2205/50; A61M
2205/82; A61M 2205/8206; A61M
2210/04; A61M 2210/0606; A61M
2210/0687; A61M 2210/06
USPC .................. 601/17; 604/20; 607/3, 62, 145
See application file for complete search history.

(56) References Cited

U.S. PATENT DOCUMENTS

| | | | |
|---|---|---|---|
| 2004/0006374 A1* | 1/2004 | Mondin | A61N 1/30 |
| | | | 607/3 |
| 2006/0062838 A1* | 3/2006 | DiPierro | A61M 37/0015 |
| | | | 424/449 |
| 2006/0116662 A1 | 6/2006 | McNichols et al. | |
| 2007/0021711 A1* | 1/2007 | Matsumura | A61N 1/044 |
| | | | 604/20 |
| 2008/0220092 A1* | 9/2008 | Dipierro | A61K 31/135 |
| | | | 424/649 |
| 2008/0243077 A1* | 10/2008 | Bivin | A61M 35/003 |
| | | | 604/131 |
| 2009/0187134 A1* | 7/2009 | Akiyama | A61K 9/0009 |
| | | | 604/20 |
| 2010/0217176 A1* | 8/2010 | Carrara | A45D 34/04 |
| | | | 604/20 |
| 2010/0274329 A1 | 10/2010 | Bradley et al. | |
| 2011/0015463 A1* | 1/2011 | Legendre | A45D 40/00 |
| | | | 600/9 |
| 2011/0082411 A1* | 4/2011 | Imran | A61N 1/30 |
| | | | 604/20 |
| 2012/0109041 A1* | 5/2012 | Munz | A45D 34/041 |
| | | | 604/20 |
| 2013/0056020 A1* | 3/2013 | Wilson | A45D 34/041 |
| | | | 132/320 |
| 2013/0204178 A1* | 8/2013 | Luzon | A61N 1/044 |
| | | | 604/20 |
| 2013/0253412 A1* | 9/2013 | Yanaki | A61N 1/303 |
| | | | 604/20 |
| 2019/0218019 A1* | 7/2019 | Beaubien | B65D 83/0894 |

FOREIGN PATENT DOCUMENTS

| | | |
|---|---|---|
| EP | 0911060 A2 | 4/1999 |
| EP | 1046407 A2 | 10/2000 |
| EP | 1944057 A1 | 7/2008 |
| EP | 2111889 A1 | 10/2009 |
| EP | 2430945 A2 | 3/2012 |
| FR | 2917299 A1 | 12/2008 |
| GB | 2372705 A | 9/2002 |
| JP | H06-070987 A | 3/1994 |
| JP | 2002-356484 A | 12/2002 |
| JP | 2007-289482 A | 11/2007 |
| JP | 2008-168081 A | 7/2008 |
| JP | 2008-220985 A | 9/2008 |
| JP | 2011-035163 A | 2/2011 |
| JP | 2012-254168 A | 12/2012 |
| WO | 2008/057640 A2 | 5/2008 |
| WO | 2009/123970 A1 | 10/2009 |
| WO | 2010/078313 A1 | 7/2010 |
| WO | 2013/187951 A1 | 12/2013 |
| WO | WO-2014027136 A1 * 2/2014 ............... A61N 1/30 |
| WO | 2015/091042 A1 | 6/2015 |

OTHER PUBLICATIONS

International Search Report for PCT/EP2014/076829, dated Feb. 6, 2015.
JP Notification of Reasons for Refusal for counterpart Application No. 2016-541369, dated Aug. 27, 2018 (translation).

* cited by examiner

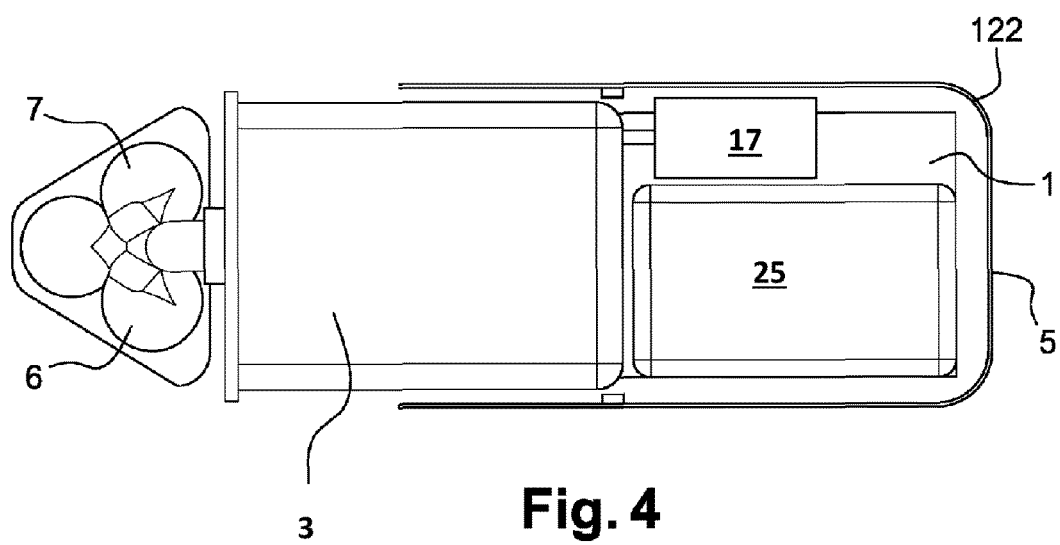
Fig. 4
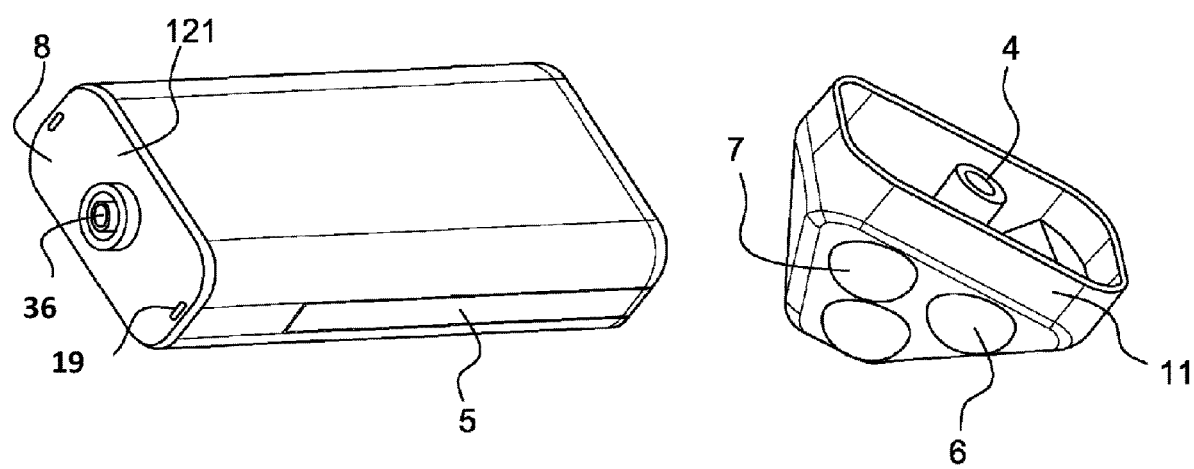
Fig. 5
Fig. 6

IONTOPHORETIC DEVICE HAVING A RESERVOIR

CROSS REFERENCE TO RELATED APPLICATION

This is a national stage application of PCT/EP2014/076829, filed internationally on Dec. 8, 2014, which claims priority to French Application No. 1363283, which was filed on Dec. 20, 2013, both of which are herein incorporated by reference in their entireties.

The present invention relates to devices for carrying out a cosmetic treatment of keratin materials, in particular of the skin, the scalp or the hair.

The expression "cosmetic product" is understood to mean any composition as defined in Council Directive 93/35/EEC of 14 Jun. 1993.

It is known that the application of an electric current to the skin can promote the penetration of active agents.

It is thus known to treat human keratin materials with the aid of iontophoretic devices (J. Singh, K. S. Bhatia, topical iontophoretic drug delivery: pathways, principles, factors and skin irritation, Med. Res. Rev., vol. 16, No. 3, 285-296, 1996).

Iontophoresis allows the diffusion of active agents through the skin by virtue of electrical stimulation in a non-invasive manner. The current applied may be adjustable in terms of intensity and direction (anodal or cathodal). The transcutaneous diffusion of the molecules via iontophoresis is based on two principles, namely electrorepulsion and electroosmosis.

Electrorepulsion is the migration of an ionized molecule by repulsion of charges of the same sign. Thus, if a substance has a positive charge, it will diffuse through the skin at the anode (+).

Electroosmosis is the migration of a molecule, even a non-ionized molecule, by entrainment associated with the flow of water from the anode to the cathode during iontophoresis. The migration is due in particular to the negative charge of the skin. Under the effect of a current, the water or a solvent entrains dissolved substances as it migrates.

The electric current can be applied to the skin by means of an end piece. For large surfaces of the body or of the cheek, the end piece may be large. In areas that are more difficult to access, the end piece may take the form of a small head that is easier to bring into contact or to move.

In order to increase the effectiveness of the iontophoresis, it is necessary to develop specific devices which optimize the penetration of the active agents through the skin.

It is already known to use an iontophoretic device provided with a massaging end piece for generating a massage that facilitates this penetration.

By way of illustration, the documents EP 2 430 945 and EP 2 111 889 describe a device for treating the contour of the eye by way of a metal ball connected to the electrode and an integrated cosmetic composition reservoir.

The patent GB 2 372 705 A describes an iontophoretic device having electrodes made of ABS plastic metallized by a corrosion-resistant metal. The reservoir is also connected to the electrode in order to ionize the formulation.

The patent U.S. Pat. No. 6,766,192 B1 describes an iontophoretic device having a ball fixed to a tube of cream.

The professional TMT® device sold by the company Bodyesthetic uses an iontophoretic device provided with a rotary ball made of stainless steel.

These devices all comprise a reservoir of product that is actuable by the user or that operates by capillary action or gravity and is more suitable for fluid formulations. It is difficult to correctly control the quantity of product delivered.

The i-beauty gun® device sold by AAMS (Anti-Aging Medical System) outputs a current via a probe of the roller type, wherein the deposition of product is regulated on the basis of the impedance measured between an electrode and the skin. With this device, the quantity of product delivered is controlled by an electronic system with a view to reducing the contact impedance with the skin.

However, in all of the currently known devices, the electrode is visible. It may be in direct contact with the skin. Consequently, the current can pass through the skin even in the absence of cosmetic composition. The effectiveness of penetration is thus not optimized.

There is thus a need for a device for cosmetic treatment with an electric current which can ensure greater effectiveness than the known devices and which can be used in complete safety.

To this end, the invention proposes disposing electrodes on an iontophoretic end piece such that said electrodes do not come into direct contact with the skin while the device is being used.

In practice, the invention proposes setting the electrodes back from the application surface so that they never touch the skin. The electrodes are located away from the application surface.

More specifically, a subject of the invention is a device for the cosmetic treatment of keratin materials with an electric current, comprising at least:
  a power supply system,
  a reservoir containing a cosmetic composition (P),
  an end piece comprising an electrode and at least one applicator member, said applicator member delimiting an outer wall that is able to be filled with product contained in the reservoir,
  a counter electrode,
  a system for regulating the quantity of composition (P) exiting the reservoir on the basis of the impedance measured between the electrode and the keratin materials, the electrode and the applicator member being designed such that the composition (P) is the only conductive substance in contact with the skin while the device is being used.

According to the invention, an "electrode" is understood to be a positively charged electrode (anode) or a negatively charged electrode (cathode). This electrode is generally disposed on the external surface of the end piece so as to come into direct contact with the keratin materials. However, the electrode may also be inserted into the external wall of the end piece. In this case, it does not come into direct contact with the keratin materials. In general, the electrode is in contact with the area to be treated.

Throughout the text, the term "electrode" means a single insulated electrode. An electrode may be in the form of a ball or pad, for example. A "counter electrode" is understood to be a negatively charged electrode (cathode) or a positively charged electrode (anode). The charge of the counter electrode is opposite to that of the electrode. In general, said counter electrode is disposed on the body of the device or on a handpiece. The counter electrode is intended to come into contact with an area of the body of the person undergoing the care treatment. For example, it may be held between the person's fingers. In one configuration, the counter electrode may be disposed on the end piece. If this is the case, it is separated from the electrodes by an insulating space.

A "power supply system" is understood to be an electrical assembly that is able to induce a potential difference between the electrodes and the counter electrode. If the end piece is placed on the face and if the counter electrode is held in a hand, the potential difference is established between the face and the hand.

The expression "the composition (P) is the only conductive substance in contact with the skin while the device is being used" means in particular that the electrode is not in contact with the skin and that the end piece does not comprise any conductive material in contact with the skin.

Preferably, the electrode is housed inside the end piece.

Advantageously, the electrode is at a distance ($d_1$) of between 0.2 mm and 5 mm from the outer wall of the applicator member.

The distance ($d_1$) represents the spacing between the electrode and the outer wall of the applicator member. This distance ($d_1$) is the shortest distance measurable between the electrode and the outer wall of the applicator member. It is measured between any point on the electrode and the outer wall of the applicator member, provided that the distance measured is the shortest distance.

Regulating System

Advantageously, the device according to the invention comprises an electronic unit designed to put the power supply of the electrodes on standby if the current detected between an electrode and the skin is below a predetermined threshold value ($i_s$). The potential difference between the electrode and counter electrode is kept at a threshold value ($U_s$) by the power supply circuit, with the power supply on standby.

By contrast, if the current ($i_m$) detected between an electrode and the skin is above this threshold value ($i_s$), the generator increases the current to a predetermined value ($I_c$) higher than $i_s$. The current flows between the electrode and the counter electrode through the skin.

More advantageously, the electronic unit comprises a current sensor for detecting the current value between the electrode and the skin.

Preferably, the threshold intensity ($i_s$) is between 5 µA and 10 µA.

Advantageously, the power supply circuit comprises a generator designed to control the voltage (U) of the electrode and the counter electrode, thereby making it possible to control the target current ($i_c$) between the electrode and the skin. The voltage (U) generated depends on the impedance ($Z_s$) of the "skin+cosmetic composition" system. It is limited to a maximum value ($U_{max}$) for safety reasons (50 V for example).

If there is not enough cosmetic composition between the electrode and the skin, the impedance (Z) is very high. The generator cannot maintain the current ($i_c$) even with the maximum voltage that it can deliver. It detects a low-intensity current.

If the quantity of cosmetic composition between the electrode and the skin increases, the generator can regain control of the current ($i_c$) on account of a decrease in the impedance ($Z_s$) at this point.

The device according to the invention may comprise an electronic unit designed to trigger the supplying of the applicator member with cosmetic composition. This triggering takes place if the current detected between an electrode and the skin is below a predetermined threshold value ($i_s$) which is slightly below the target value ($i_c$).

Just after this triggering takes place, the current intensity ($i_m$) measured increases to a target value ($i_c$). As soon as it reaches this target value ($i_c$), the supplying of the applicator member with cosmetic composition is automatically interrupted.

Preferably, the power supply circuit comprises a microcontroller.

In practice, the intensity between the electrode and the skin is maintained between the threshold intensity ($i_s$) and the target intensity ($i_c$) by the power supply circuit.

The current ($i_m$) is compared with the threshold intensity value ($i_s$) and the target intensity value ($i_c$) by a microprocessor.

If ($i_m$)<($i_s$), then the supplying of the applicator member with cosmetic composition is triggered. This supplying continues until a current equal to the predetermined value ($i_c$) is detected.

If ($i_m$)≥($i_c$), then the supplying of the applicator member with cosmetic composition is interrupted. There is then a situation of saturation of formulation.

Preferably, the current ($i_c$) is identified in order to reach a current intensity per unit area that ranges from 0.01 mA/cm$^2$ to 0.5 mA/cm$^2$, preferably from 0.1 mA/cm$^2$ to 0.3 mA/cm$^2$.

It will be understood that the term "microcontroller" corresponds to a single electronic device, for example a microprocessor chip, or to a set of programmable electronic elements, for example communication gateways that allow management by a third party item of equipment (such as a PC, PDA, etc.).

Electrical Parameters

The electrical power source may comprise any non-rechargeable battery or any storage battery. The voltage between the electrodes is for example between 1.2 V and 24 V, preferably between 1.2 and 3.3 V. If appropriate, the passage of the current can create spot heating.

The electrical power source may comprise, for example, a DC voltage source. In a variant, the electrical power source may comprise an electronic circuit for varying the amplitude of the voltage generated over time. This electronic circuit may be a chopper, for example.

At an equivalent current density, the device can in particular deliver a current density, at the skin, of preferably less than or equal to 0.500 mA/cm$^2$, for example between 0.01 mA/cm$^2$ and 0.500 mA/cm$^2$, for example between 0.1 mA/cm$^2$ and 0.3 mA/cm$^2$.

Electrode

The electrode may be flat, for example in the form of a flat disc or polygon.

The electrode may be porous.

The electrode may be hollow, being formed for example by stamping or bending an electrically conductive metal sheet.

Materials Able to be Used to Produce the Electrodes

The electrode may comprise, for example:
- a metal (chromium, stainless steel), for example
- a noble metal (gold, titanium) which is inert with respect to the formulation,
- a metal plated with a noble metal,
- an alloy,
- a composite material (plastics material loaded with carbon microfibres),
- a conductive woven fabric,
- a conductive nonwoven fabric,
- a polymer material rendered conductive,
- a fibrous material,
- conductive polymeric fibres, for example as described in the publication CN101532190,
- carbon fibres, for example as described in the publication JP2009179915, silicones rendered conductive by the addition of conductive fillers such as silver, copper or carbon. Such silicones are supplied, for example, by the companies Saint Gobain, Plastics Performance and Aquitaine Caoutchouc 2000, conductive metallic fabrics, supplied for example by the companies Utexbel and Cousin Biotech, carbon-loaded vinyl, supplied for example by the companies Copema and Rexam, electrosurgical plates, supplied for example by the companies Copema and 3M, intrinsically conducting polymers, supplied for example by the company Paniplast.

Applicator Member

The applicator member may have any desired geometric shape.

It is neither conductive nor connected to the power supply circuit.

Advantageously, the device comprises a plurality of applicator members.

The outer wall of the applicator member may be completely inert from a chemical point of view with respect to the products and keratin materials.

The outer wall may be covered with a varnish.

The outer wall may be polished.

The outer wall may comprise a biocidal material.

Advantageously, the applicator member can rotate about a rotation axis.

Furthermore, the outer wall of the applicator member may be disposed in the vicinity of the product reservoir, thereby making it possible to avoid the presence in particular of specific ducts for transporting the product from the reservoir to this outer wall.

In one implementation example of the invention, the outer wall is substantially rotationally symmetrical about an axis of symmetry, the outer wall being able to rotate about this axis of symmetry.

In a variant, the applicator member may be able to rotate about a rotation axis separate from this axis of symmetry.

The outer wall of the applicator member may have a substantially elongate ellipsoidal shape or, in a variant, a substantially flattened ellipsoidal shape.

In another implementation example of the invention, the outer wall has a substantially spherical shape (roll-on). In particular, the applicator member is a ball.

The applicator member may comprise a core to which the outer wall is attached. This core may comprise for example a surface provided with reliefs and the outer wall may be able to deform during application so as to come into contact with the reliefs. The latter make it possible to produce a massaging effect while the applicator member is in contact with the surface to be treated, this being able, among other things, to facilitate the penetration of the product into the skin and to promote its action.

In a variant, the outer wall may be rigid.

In one implementation example of the invention, the outer wall comprises reliefs, which may comprise for example bosses or ribs.

Alternatively, the raised elements may be removable. It is thus possible to change the raised elements of the device, for example in order to modify their dimensions, their surface properties, or else their roughness.

Advantageously, the applicator member is mounted in a removable manner on the device.

More advantageously, the applicator member comprises at least one relief.

Reservoir

The reservoir may comprise a wall at which the outlet orifice emerges, this wall substantially following the shape of at least a portion of the applicator member.

The mechanism for dispensing the formulation at the outlet of the reservoir may comprise a pump.

Advantageously, the dispensing system comprises an air pump so as to compress the air between the walls of the reservoir and its housing. The walls of the reservoir are preferably flexible and the walls of the housing are preferably rigid.

More advantageously, the housing is airtight. The reservoir is compressed in a controlled manner by the air pump. This creates a certain pressure in the housing in order to make the flow rate of the formulation regular. A unidirectional valve at the end of the reservoir can make it possible to preserve the formulation from contact with the air.

When the current generator detects a drop in current, it can activate the pump in order to push the formulation out of the reservoir. The impedance is thus re-balanced. This principle makes it possible to ensure a sufficient quantity of composition between the electrode and the skin. It makes it possible to optimize the penetration of the composition.

The reservoir may have a variable internal volume and comprise at least one wall that is elastically deformable so as to reduce the internal volume, in particular two elastically deformable walls opposite one another.

The reservoir may be designed to be mounted in a removable manner on the device such that, when the reservoir has been emptied, it can be replaced with another or removed in order to be filled, when the reservoir has a filling orifice.

Advantageously, the reservoir has an elastically deformable outer wall.

Preferably, the reservoir comprises an outlet orifice that emerges through a duct at the external wall of the applicator member.

Advantageously, the deformable region is an axially deformable region.

An "axially deformable region" is understood to be a region that is deformable along the head wall of the end piece.

Advantageously, the deformable region comprises a bellows.

This thickness of the bellows is for example between 0.1 mm and 1 mm, and preferably between 0.3 mm and 0.8 mm.

Advantageously, the number of folds in the bellows may be between two and six, better still between three and five.

Advantageously, the reservoir is formed in one piece.

It is preferably moulded in one piece, in particular from the same thermoplastic material, for example LDPE, HDPE, a mixture of LDPE and HDPE, PP or a mixture of PE and PP in any proportion. The thickness of the wall of the reservoir is for example between 0.1 and 1 mm, and in the second region between 0.3 and 0.8 mm.

Advantageously, the total internal volume of the reservoir is between 1 and 100 $cm^3$, preferably between 20 and 50 $cm^3$, in the rest configuration of the deformable region. This volume is optimal for a number of uses or repeated treatment over a number of weeks.

Preferably, the internal volume of the reservoir can diminish by a volume of between 10% and 50% of the internal volume of said reservoir in the rest configuration of the deformable region. This variation in volume has the advantage of being visible and measurable.

The reservoir may be manufactured by injection blow moulding or extrusion blow moulding.

Advantageously, the reservoir is removable.

More advantageously, the reservoir is a single-use reservoir.

It may or may not be a single-dose reservoir.

Supplementary Functions

The device may comprise one or more treatment modules which can be activated selectively, for example it is conceivable to subject the end piece to light, to a source of heat, or even to vibrations, as will be explained in detail below.

i) Source of Light

According to the invention, the device advantageously comprises a source of light.

The source of light may be, for example, at least one LED, as described in the documents FR-A-2 917 299, US-A-2010/274329 or WO-A-2008/057640.

ii) Source of Heat

According to the invention, the device advantageously comprises a source of heat.

In this case, it is possible to modify the temperature of the external surface of the end piece and/or of the region treated and/or to transmit energy to the external surface of the end piece and/or to the region treated.

The device may comprise for example a heating resistor or a thermoelectric element or an infrared source which is positioned under the end piece.

Preferably, the source of heat comprises an infrared source or a resistor.

The device may comprise a heating module and be configured to heat the external surface of the end piece to a predefined temperature, for example to a temperature of between 35° C. and 45° C. In the case of a device comprising a heating module, the heating surface can reach a temperature of 10° C. to 35° C. greater than room temperature, preferably of 15° C. to 25° C. greater in heating mode. The power delivered by the heating module may be between 0.25 and 10 W, preferably between 0.5 and 5 W.

More preferably, the source of heat is housed entirely inside the device.

The resistor may be connected to a board by two insulated connectors, using for example the location of the switches.

The infrared source may be integrated into the body of the device, such as the handle. The external part of the device, for example a shell, can serve to guide the infrared radiation towards the end piece.

The electrical circuit may comprise at least one electronic switch which is connected in series with the heating member and makes it possible for example to supply it with power at the desired ratio.

Cosmetic Compositions

It is possible to use at least one cosmetic composition with the device.

The composition(s) used may be in all forms, for example in the form of an aqueous solution, of an oil, of an emulsion, of a powder or of a gel. The composition(s) used may also be sprayed onto the skin.

When the composition(s) used is/are in the form of a gel, the latter can take on the shape of the electrode to which it is applied, as mentioned above.

The composition(s) may comprise an active principle.

Advantageously, the cosmetic product is chosen from:
- a face care or body care composition, comprising in particular an active agent chosen from humectant or moisturizing active agents, anti-ageing active agents, for example depigmenting active agents, active agents that act on cutaneous microcirculation or seboregulating active agents,
- a composition for making up the face or body,
- a hair composition, in particular a composition for washing the hair, for hair care or conditioning, for temporary form retention or shaping of the hair, for the temporary, semi-permanent or permanent dyeing of the hair, or for relaxing or permanent-waving, in particular a composition for relaxing, dyeing or bleaching the roots and hair, and
- a composition for the scalp, in particular an antidandruff composition, a composition for preventing hair loss or for promoting regrowth of the hair, an anti-seborrheic composition, an anti-inflammatory composition, an anti-irritation or soothing composition, a mark-preventing composition or a composition for stimulating or protecting the scalp.

The device can be used in various cosmetic treatments, for example for combating wrinkles, herpes, acne or for redensifying the skin or the hair.

BRIEF DESCRIPTION OF THE DRAWINGS

Further features and advantages of the present invention will become apparent on reading the following detailed description, which is given with reference to nonlimiting embodiments that are illustrated in the appended drawings, in which:

FIGS. 1 to 6 show a device in accordance with the invention. It comprises a body 12 on which there is mounted an end piece 2 comprising two applicator members 6 and 7 and an electrode 4. A product reservoir 3 is housed inside the body 12.

Figure 1:
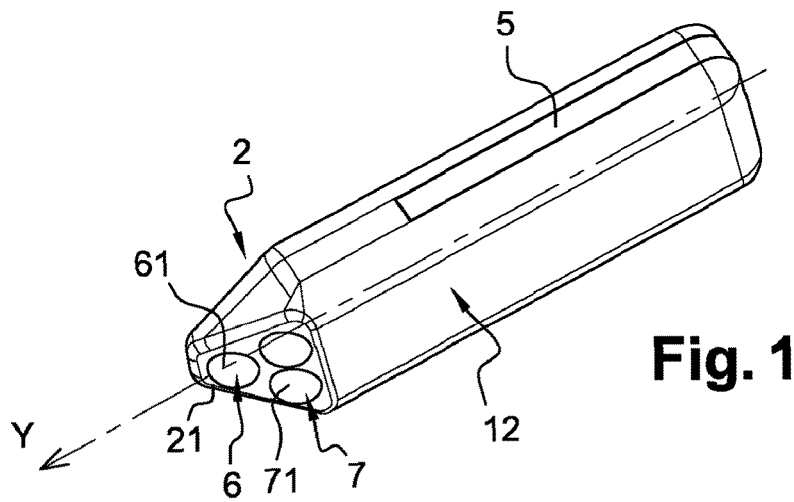
FIG. 1 schematically and partially illustrates a perspective view of a device in accordance with the invention, FIG. 2 schematically and partially illustrates the device from FIG. 1, in axial section, FIG. 3 schematically and partially illustrates a side view of the device from FIG. 1, FIG. 4 schematically and partially illustrates a top view of the device from FIG. 1, FIG. 5 schematically and partially illustrates a perspective view of the device from FIG. 1, with the end piece detached, FIG. 6 schematically and partially illustrates a perspective view of an end piece of the device from FIG. 1.

The device is supplied with power by a current generator 1 (electronic board). This generator 1 is supplied with power by a battery 25 (non-rechargeable or rechargeable battery).

It can deliver:
- a constant DC current I programmed for an iontophoresis mode (+ or −) or
- electric pulses for an electroporation mode or
- a constant DC current I coupled with electric pulses V from time to time for an ionto-stimulation mode. The duration and frequency of these pulses are programmable.

The polarization of an electrode 4 and that of a counter electrode 5 are reversible (+ or −) depending on the nature of the cosmetic composition (P) used.

The device also comprises a system for regulating the quantity of composition (P) exiting the reservoir 3 on the basis of the impedance measured between the electrode 4 and the keratin materials. The operation of this system is known per se.

In the example in question, the body 12 is made of thermoplastic material. In a variant, it can be made of any other material.

In the example in question, the applicator members are balls (roll-on) made of plastics material. They are mounted on the shell 11 of the end piece 2. The applicator members 6 and 7 could have any other shape, for example that of rollers.

In its upper part, the body 12 comprises a head 121 extending along an axis Y and intended to receive the end piece 2.

The end piece 2 is clip-fastened to the head 121 of the body 12. It could be mounted in some other manner.

Figure 2:
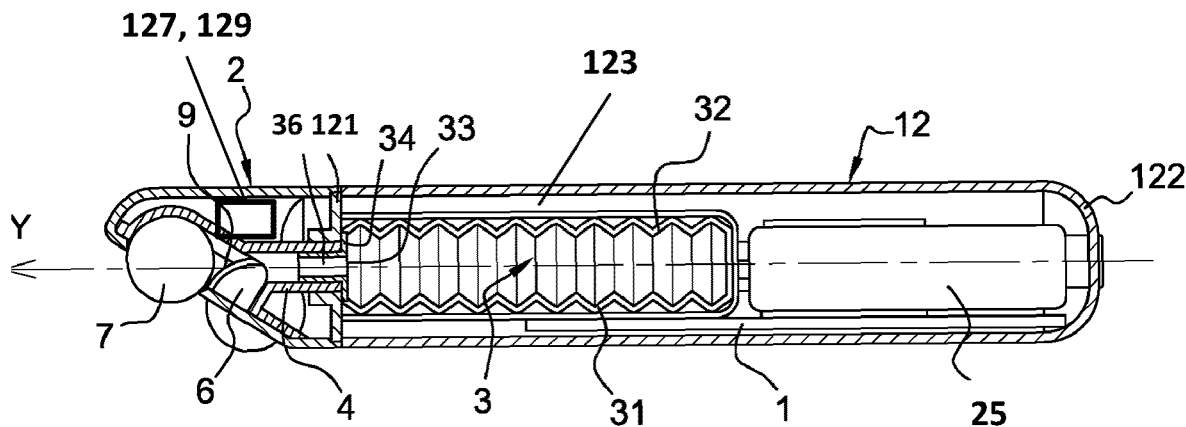
Figure 3:
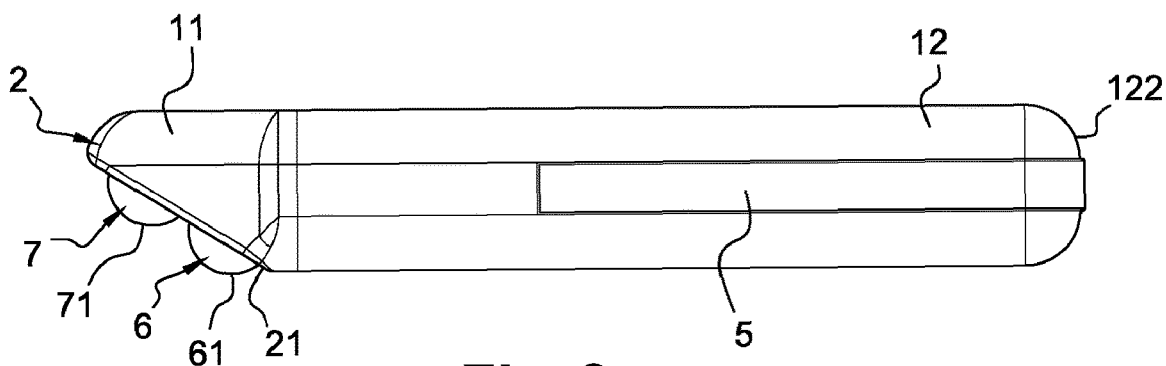

The body 12 comprises an end wall 122 having a substantially concave shape, as can be seen in FIG. 2.

The end piece 2 is made up of three parts: the electrode 4, the balls 6 and 7 and the shell 11. The shell 11 is removable to facilitate cleaning after use. The electrode 4 is connected to one pole of the electric current generator 1. It communicates with the reservoir 3 in order to ensure the transmission of electric current to the cosmetic composition. The cosmetic composition is ionized on exiting the reservoir 3. It then passes over the balls 6 and 7 in order to reach the skin for the purpose of an iontophoretic and/or electroporation treatment. In some embodiments, the device may include a source of light 127 and/or a source of heat 129, which may include a resistor or an infrared source.

The counter electrode 5 is disposed on the external face of the body 12. It is connected to the other pole of the current generator 1. The counter electrode 5 makes it possible to close the circuit at the time of the treatment. The electric current generated passes through a connector 8. The latter is placed on the head 121 of the body 12. It is thus joined to the electrode 4. Finally, it conveys the ionized formulation into the space 9 and around the balls 6 and 7. The current then reaches the skin before returning to the counter electrode 5, passing through the hand holding the device.

In this configuration, the electrode 4 is not in direct contact with the skin. It is housed entirely inside the end piece 2. If there is not enough composition between the electrode 4 and the skin to close the circuit, the current generator 1 detects an increase in impedance. It activates a pump to push the composition out of the reservoir through the ionization system in order to re-balance the level of impedance. This principle makes it possible to ensure a sufficient quantity of composition between the electrode 4 and the skin and optimizes the penetration of the composition.

The end piece 2 defines openings in its head wall 21 so as to leave free approximately half of the applicator members 6 and 7.

Each applicator member 6 and 7 is held on the end piece 2 so as to rotate freely about a core, in a manner known per se (roll-on).

The applicator members 6 and 7 also comprise an outer wall 61 and 71 that is able to be filled with product contained in the reservoir 3 and has a spherical shape in the example in question.

The reservoir 3 is fitted in a removable manner between the walls of a housing 123 in the body 12. It is extended by a duct 36.

The reservoir 3 is in the form of a bellows. It defines a variable internal volume and has two elastically deformable walls 31 and 32 that are disposed opposite one another, as illustrated in FIG. 4.

This reservoir 3 is compressed in a controlled manner by an air pump system 17 which creates a certain pressure in the shell and makes the flow rate of the formulation regular. A unidirectional valve at the end of the reservoir also makes it possible to preserve the formulation from contact with the air.

The reservoir 3 comprises an end wall 34 provided with one or more outlet orifices 33. This outlet orifice 33 may be circular or in the form of a slot for example.

The reservoir 3 may comprise, on its lateral sides, two longitudinal grooves that are each intended to engage with two corresponding longitudinal ribs on the housing 123.

When the reservoir 3 is in place on the body 12, the end wall 34 of the reservoir 3 is positioned against the head 121 of the body 12.

The conductive material used for the electrode 4 may be metal or conductive plastics material or graphite and preferably have a chemically inert nature with respect to the formulation (e.g. gold, platinum, or gold-plated metal, graphite, vitreous carbon, plastic or elastomer or silicone filled with carbon fibre).

In another configuration of the device, a single-dose package in the form of a capsule having flexible membranes can be used to replace the reservoir 3.

The device is separable into two parts: the body 12 and the end piece 2. When the end piece 2 is fastened to the body 12, the connector 8 makes it possible to connect the electrode 4 to one pole of the generator 1 housed in the body 12.

The composition reservoir 3 may be preserved by a cap, in the body 12.

One or more switches 19 make it possible to detect the presence of the end piece 2 in order to ensure the safety of the device. If the end piece 2 is present, it is possible to start the treatment, if the end piece 2 is not present, the body 12 is deactivated.

The reservoir 3 contains a cosmetic product, for example a gel or a liquid, in particular a low-viscosity liquid.

In order to start the treatment, the user starts up the device, causing the balls 6 and 7 to rotate.

In contact with the surface to be treated, said balls produce a massaging effect on the surface.

The outer walls 61 and 71 are filled with product.

As soon as the impedance measured between the skin and the electrode 4 is too high, the pump activates the outlet of the product.

The device outputs a current with the deposition of product being regulated on the basis of the impedance measured.

The electrode 4 is not in contact with the skin.

The non-conductive balls 6 and 7 are always covered with cosmetic composition while the appliance is in operation.

The composition is the only conductive substance in contact with the skin while the device is being used.

The present invention has been described with reference to particular embodiments that are illustrated in FIGS. 1 to 6, and with reference to particular examples, but it will be understood that further variants may be envisaged by a person skilled in the art, in particular the number and types of electrodes may vary and other arrangements than those described may be envisaged in order to form appliances according to the invention. In particular, the shape of the end piece may vary or the position of the electrodes and the counter electrode. The latter may be disposed on the end piece for example. The device may have an angled shape such that the longitudinal axis Y of the body 12 makes an angle with the head wall 21 of the end piece 2 of 30° for example.

The expression "comprising a" should be understood as being synonymous with "comprising at least one", unless specified to the contrary.

The invention claimed is:

1. A device for the cosmetic treatment of keratin materials with an electric current, comprising:
   a reservoir containing a cosmetic composition;
   an end piece configured to receive the cosmetic composition from the reservoir;
   an applicator member disposed in the end piece, such that a portion of the applicator member is exposed outside of the end piece and configured to contact the keratin materials;
   a first electrode disposed in the end piece and configured to transmit an electric current to the cosmetic composition disposed on the applicator member;
   a counter electrode;
   a current generator configured to generate an electric potential between the first electrode and the counter electrode and measure an impedance between the first electrode and the keratin materials; and
   a dispensing system configured to regulate an amount of the cosmetic composition that is dispensed from the reservoir onto the applicator member, based on the measured impedance,
   wherein the first electrode and the end piece are configured such that the first electrode is prevented from directly contacting the keratin materials while the device is being used.

2. The device according to claim 1, wherein the first electrode is at a distance ($d_{min}$) of between 0.2 mm and 5 mm from the applicator member.

3. The device according to claim 1, wherein the applicator member can rotate about a rotation axis.

4. The device according to claim 1, wherein the applicator member is a ball.

5. The device according to claim 1, wherein the reservoir has an elastically deformable outer wall.

6. The device according to claim 1, wherein the reservoir comprises a duct configured to supply the cosmetic composition to the end piece.

7. The device according to claim 1, wherein the applicator member further comprises a plurality of applicator members.

8. The device according to claim 1, further comprising a source of light.

9. The device according to claim 1, further comprising a source of heat.

10. The device according to claim 9, wherein the heat source comprises an infrared source or a resistor.

11. The device according to claim 1, wherein the reservoir is removable.

12. The device according to claim 1, wherein the reservoir is a single-use reservoir.

13. The device according to claim 1, wherein the cosmetic composition is chosen from:
   a face care or body care composition;
   a composition for making up the face or body;
   a hair treatment composition; or
   a composition for the scalp of a user.

14. The device according to claim 1, wherein the cosmetic composition is a face care or body care composition having an active agent chosen from humectant or moisturizing active agents, anti-ageing active agents, active agents that act on cutaneous microcirculation, or seboregulating active agents.

15. The device according to claim 14, wherein the anti-ageing active agent comprises a depigmenting agent.

16. The device according to claim 1, wherein the cosmetic composition is a hair treatment composition chosen from:
   a composition for washing the hair, for hair care or conditioning, or for temporary form retention or shaping of the hair;
   a composition for temporary, semi-permanent, or permanent dyeing of the hair; or
   a composition for relaxing or permanent-waving the hair.

17. The device according to claim 1, wherein the cosmetic composition is a composition for the scalp of a user chosen from an antidandruff composition, a composition for preventing hair loss or for promoting regrowth of the hair, an anti-seborrheic composition, an anti-inflammatory composition, an anti-irritation or soothing composition, a mark-preventing composition, or a composition for stimulating or protecting the scalp.

* * * * *